United States Patent [19]

Schwarze et al.

[11] 4,061,869

[45] Dec. 6, 1977

[54] ANTISTATIC AGENT FOR THERMOPLASTIC SYNTHETIC RESIN

[75] Inventors: Werner Schwarze, Frankfurt; Wolfgang Merk; Volker Binder, both of Hanau, all of Germany

[73] Assignees: Deutsche Gold- und Silber-Scheideanstalt vormals Roessler, Frankfurt; Henkel U. Cie, Dusseldorf-Holthausen, both of Germany

[21] Appl. No.: 687,632

[22] Filed: May 18, 1976

[30] Foreign Application Priority Data

May 20, 1975 Germany .............................. 2522287

[51] Int. Cl.² ...................... C08L 23/06; C08L 23/12; C08L 25/06; C08L 27/06
[52] U.S. Cl. .................................. 526/1; 260/31.8 R; 260/33.2 R; 260/42.53; 260/614 R; 260/615 B; 428/442
[58] Field of Search ........... 526/1; 260/614 R, 615 B, 260/42.53

[56] References Cited

U.S. PATENT DOCUMENTS

| | | | |
|---|---|---|---|
| 2,236,919 | 4/1941 | Reynhart | 260/635 |
| 3,240,819 | 3/1966 | Gaertner et al. | 260/615 |
| 3,607,778 | 9/1971 | Lincoln et al. | 252/353 |
| 3,931,338 | 1/1976 | Rupilius | 260/615 R |
| 3,954,884 | 5/1976 | Kidwell | 260/615 R |

FOREIGN PATENT DOCUMENTS 1,023,524  3/1966  United Kingdom ................ 526/1

Primary Examiner—Stanford M. Levin
Attorney, Agent, or Firm—Cushman, Darby & Cushman

[57] ABSTRACT

There are prepared compounds of the formula

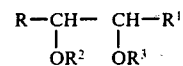

where
R and R¹ are saturated and preferably linear alkyl groups in which the sum of carbon atoms in the two alkyl groups is 4 to 30,
one of R and R¹ can also be hydrogen,
R² is hydrogen or if R³ is hydrogen, then
R² is the group

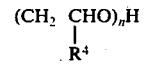

where $n$ is 1 to 10,
R³ is hydrogen or, if R² is hydrogen, then
R³ is the group

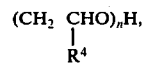

and
R⁴ is hydrogen or methyl.

The compounds are useful as antistatic agents for thermoplastic resins.

18 Claims, No Drawings

ANTISTATIC AGENT FOR THERMOPLASTIC SYNTHETIC RESIN

The electrostatic charging of thermoplastic synthetic resins as for example polyolefins, e.g. polyethylene and polypropylene, polystyrene, polyvinyl chloride, nylon and polymethyl methacrylate leads to known difficulties in their production, working and in the use of the products therefrom as films, fibers, sheets, tubes and other shapes as well as lacquers and varnishes.

The charging with static electricity can be prevented or reduced by materials which are applied to the surface of the synthetic resin. These materials are designated as external antistatic agents. However, the thin layer produced is effective only so long as it is not mechanically removed from the surface, for example by wiping off, abrading, washing or the like. Substantially more permanent is the effect of material which are added to the synthetic resin before the processing. Materials used for this purpose are called internal, antistatic agents. These should at the same initial antistatic effect exhibit a longer-lasting effect, be effective at the lowest possible concentration, be odorless and have the least possible toxicity. Furthermore they should not lead or contribute to the gluing together of the surfaces of synthetic resin products and they should not have a negative influence on the thermal stability, color, transparency, mechanical properties or properties in use of the synthetic resin. Especially it is required that the antistatics do not change the properties of other synthetic resin additives, e.g. antioxidants and UV absorbants and that the working properties of the synthetic resins are not impaired. Therefore the problem of the invention was to find materials which could by synthesized from easily accessible material at slight industrial expense which satisfy these high requirements for antistatic agents, particularly materials which can be used as internal antistatics.

It has now been surprisingly found that compounds of the formula

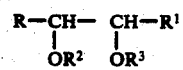

I where
R and R¹ are saturated and preferably linear alkyl groups in which the sum of carbon atoms in the two alkyl groups is 4 to 30,
one of R and R¹ also can be hydrogen,
R² is hydrogen or, if R³ is hydrogen, then
R² is the group

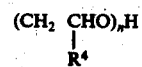

where $n$ is 1 to 10,
R³ is hydrogen or, if R² is hydrogen, then
R³ is the group

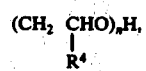

and
R⁴ is hydrogen or methyl, are especially well suited as agent for antistatically equipping thermoplastic synthetic resins, particularly as internal (inner) antistatic agents.

The named groups R and R¹ are preferably linear alkyl groups and in the sum possess 4 to 20 carbon atoms R⁴ is preferably hydrogen, $n$ is preferably 1 to 4.

These compounds can be produced by methods known in themselves. As starting materials there are used terminal or inner epoxides which are easily accessible from industrial olefins. Thus, there can be used 1,2-epoxides such as 1,2-epoxyhexane, 1,2-epoxyoctane, 1,2-epoxynonane, 1,2-epoxydecane, 1,2-epoxydodecane, 1,2-epoxyhexadecane, 1,2-epoxyoctadecane, 1,2-epoxyeicosane, 1,2-epoxytetracosane, 1,2-epoxytriacontane, 2,3-epoxydodecane, 5,6-epoxydodecane, 7,8-epoxyoctadecane, 9,10-epoxyoctadecane, 10,11-epoxyeicosane. The epoxides are reacted under acid or alkaline catalyst conditions with ethylene glycols, e.g. ethylene glycol, diethylene glycol, triethylene glycol, tetraethylene glycol, pentaethylene glycol, hexaethylene glycol, octaethylene glycol or decaethylene glycol or with 1,2-propylene glycols, e.g. propylene glycol, dipropylene glycol, tripropylene glycol, tetrapropylene glycol, hexapropylene glycol or decapropylene glycol. As catalysts there are suited for example BF etherate, sulfuric acid, sodium methylate, lithium methylate, etc. Among the ethylene or propylene glycols there are preferably named the mono-, di-, tri-and tetraethylene - or propylene glycols.

The above mentioned methods of production are addition reactions and the methods as such are known in the literature, e.g. K. Shibata and S. Matsuda, Bull. Jap. Petrol. Inst. Vol. 7, pages 25–30 (1965); Houben-Weyl Vol. VI/3, pages 42–44; R. E. Parker and W. S. Isaacs, Chem. Rev. Vol. 59, pages 737–799 (1959) and the methods shown in such literature can be employed replacing the reactant, e.g. an amine, with an ethylene glycol or propylene glycol.

Thus by these arise by reaction of terminal epoxides and ethylene glycols under alkaline conditions exclusively monoadducts of the structure

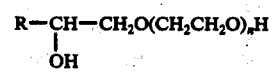

II while with acid catalysts mixtures are formed which beside compounds of the above structure II also contain compounds of the isomeric structure

III

In both addition reactions there are formed by-products such as diadducts of the formula

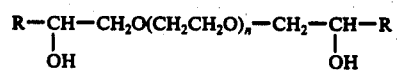

IV

Both types of the above named monoadducts show comparable antistatic activity while the diadducts either are not antistatically active or are active to only a slight extent. However, it has been found that monoadducts which contain corresponding amounts of diadducts exhibit practically the same antistatic activity as the pure monoadducts. So, for attaining the antistatic activity of the invention it is not necessary to purify the material obtained from the described reactions, unless it is desired for other reasons. They can thus be added as crude products as they occur after separation of the catalysts and in a given case the solvent.

The name compounds are excellent antistatic agents for thermoplastic agents as chemical individuals, as mixtures with each other or as mixtures with silica or silica gel, especially with pyrogenically produced, preferably pure highly dispersed silica, preferably as so-called inner antistatic agents.

An advantageous modification of the agent of the invention consists of at least one antistatic agent according to the above general formula I in an amount of 0.1 to 20 parts by weight in admixture with a thermoplastic synthetic resin in an amount of 100 parts by weight in homogeneous distribution. This mixture furthermore can contain silica in an amount of 0.1 to 40 parts by weight as well as in a given case other known additives for synthetic resins in customary amounts. Among these there may be mentioned particularly other fillers such as silica, silicates, clay, chalk (calcium carbonate), carbon black, etc., dyes, pigments, plasticizers, propellants (foaming agents), lubricants, stabilizers against the effects of light, heat, oxygen, ozone, etc., antiblocking agents and the like known additives for thermoplastic synthetic resins.

The new antistatic agents are outstandingly suited on or in thermoplastic synthetic resins, especially in high pressure polyethylene, low pressure polyethylene, polypropylene, polystyrene, polyvinyl chloride, polyvinyl acetate, polybutadiene, polymethacrylates, e.g. polymethyl methacrylate and in copolymers of ethylene with propylene, ethylene with vinyl acetate as well as styrene with acrylonitrile. Other thermoplastic polymers include chlorinated polyethylene, chlorinated polypropylene, polyacrylonitrile, acrylonitrile-vinyl acetate copolymer, acrylonitrile-vinyl chloride copolymer, vinylidene chloride-acrylonitrile copolymer, vinylidene chloride-vinyl chloride copolymer, polyvinylidene chloride, vinyl chloride-vinyl acetate copolymer, polyvinyl acetate, polyvinyl acetals, e.g. polyvinyl butyral, polyvinyl ethers, e.g. polyvinyl methyl ether, polyvinyl ketones, e.g. polyvinyl methyl ketone, nylon 6, nylon 6, 6, nylon 6, 10, nylon 11, nylon 12, linear polyesters, e.g. polyethylene terephthalate, linear polyurethanes, polyoxymethylene, polycarbonates, cellulose acetate, cellulose butyrate, cellulose acetate-propionate cellulose acetate-butyrate, etc. They are preferably employed with polyolefins and polyvinyl chloride, particularly plasticized polyvinyl chloride, namely in amounts of 0.01 to 5%, preferably 0.1 to 3% based on the weight of the synthetic resin, whereby, particularly at optimum concentration, there is obtained at once its antistatic activity which for most materials reaches their maximum value after 24 hours. The antistatic agents can be well worked into thermoplastic synthetic resins, do not impair the working properties of the synthetic resins, as for example, the bonding properties, do not effect any adhesiveness, are stable under the working conditions, are only to a very slight extent washed out of the polymers by water and regenerate their optimum activity within several days.

It has proven especially advantageous that the antistatic agents of the invention on the one hand only migrate in such manner from the synthetic resin to the surface that the concentration of the antistatic is sufficient to reduce the surface resistance in an optimum manner, for example from $10^{14}$ ohms (a value, which is measured in most synthetic resins not supplied with an antistatic agent) to $10^8$ to $10^{10}$ ohms, and on the other hand a sufficient effect occurs immediately after the processing of the synthetic resin. The new antistatic agents in general are without disturbing odor and either do not influence the mechanical and thermal properties of the synthetic resin or only have an insignificant effect.

The anitstatic agents of the invention can be brought into the thermoplastic synthetic resin in various ways. For example, the synthetic resin can be worked with the antistatic agent to a homogeneous mass in a commercial mixer. The antistatic agents can be incorporated as a solution, dispersion, suspension or emulsion in a suitable solvent, for example methanol or chloroform into the synthetic resin present as granulate, chips or powder. After strong stirring of the mixture and drawing off of the organic solvent the synthetic resin is shaped by customary processes, for example on mixing rolls with heated rolls or in an extruder. The antistatic agents, however, can also be worked into the synthetic resin directly on the rolls or in an extruder. Furthermore there can be mixed into the synthetic resin a higher amount of antistatic agent than is desired and thus produce a so-called master batch, which in a given case in another operation can be brought to the desired above given final concentration of antistatic in a second working step with additional synthetic resin.

The antistatic agents of the invention are also excellently effective as external additives for the synthetic resins.

It could not be foreseen that the antistatic agents of the invention could be mixed without difficulties into those polymers which are processable by extrusion techniques even in relatively high concentrations, as is desired in the production of the master batches, namely without the use of assistants which make the processing easier and without the formation of the feared smearing effect which otherwise can take place in extrusion processes through an increasing glide effect.

If desired there can also be worked into the master batch advantageously at the same time other synthetic resin additives necessary for the later processing of the synthetic resin and needed for the use of the synthetic resin product as for example antiblocking agents, heat and light stabilizers, pigments, dyestuffs, plasticizers, lubricants, fillers, glass fibers and other polymers.

The examination of the antistatic agents has advantageously shown that the tested materials have a decidedly small toxicity. Thus the acute oral toxicity of the antistatic agent of Example (b) (crude product) in rats in $LD_{50} = 11.6$ ml/kg orally, which is about 11 grams per kilogram of body weight.

The good antistatic activity of the new antistatic agents in thermoplastic synthetic resins as well as their problem-free incorporation in the same are surprising since the chemically very similarly contructed oxethylates of alkanols (see Browning Great Britain patent specification No. 731,728) according to a statement in Rombush U.S. Pat. 3,708,464 on col. 2 lines 36–42 are inclined to exude from the synthetic resin when employed in antistatically effective concentrations. Compounds produced from epoxides according to Braus U.S. Pat. No. 3,308,111, Braus U.S. Pat. No. 3,317,505 and Adams U.S. Pat. No. 3,365,435 which should impart antistatic properties to thermoplastic synthetic resins, as can be seen from the following use Example 1

(see Table 2, in comparison with the values of Table 1) have only a slight effect. Furthermore there are known antistatic thermoplastic synthetic resins in which as antistatically effective compounds there are used condensation products starting from glycerol (2,3-epoxypropanol-1) (Wirth, German Offenlegungsschrift No. 2,324,888). As can be seen from the values of subsequent Table 2 in combination with use Example 1 such materials are clearly below the antistatic agents of the invention in their activity.

Unless otherwise indicated all parts and percentages are by weight.

PRODUCTION EXAMPLES

EXAMPLE (a)

In a three necked flask equipped with a thermometer, stirrer and reflux condenser there were heated to 170° C with stirring 184 grams of 1,2-epoxydodecane, 106 grams of diethylene glycol and 1.4 grams of sodium methylate. After the subsiding of the exothermic reaction the reaction mixture was held at 170° C for another 2 hours. After cooling to 100° C it was poured into acidified water (acidified with hydrochloric acid), the organic phase extracted wih diethyl ether, the ethereal solution washed neutral with water and the ether driven off. There were obtained 250 grams of crude product as a yellowish, pasty material.

By rectification of the crude product there was obtained as distillate 160.5 grams of the monomeric compound

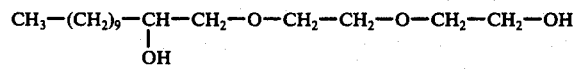

as a viscous, colorless liquid having a B.P.$_{0.2}$ of 166°–170° C and as sump 86.3 grams of the dimer compound

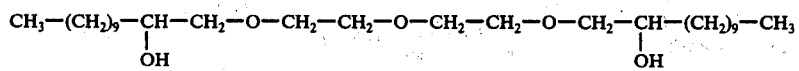

which after recrystallization from petroleum ether was present as colorless crystals having a M.P. 58°–59° C.

The analysis of the monomer compounds gave the empirical formula $C_{16}H_{34}O_4$ and the following values

|  | % C | % H |
|---|---|---|
| Found | 66.2 | 11.9 |
| Calculated | 66.2 | 11.8 |

The analysis of the dimer compound gave the empirical formula $C_{28}H_{58}O_5$ and the following values

|  | % C | % H |
|---|---|---|
| Found | 71.2 | 12.4 |
| Calculated | 70.9 | 12.4 |

EXAMPLE (b)

In a three necked flask equipped with a thermometer, stirrer and reflux condenser there were heated at reflux with stirring for 2 hours 184 grams of 1,2-epoxydodecane, 318 grams of diethylene glycol, 0.95 gram of boron trifluoride etherate and 620 ml of benzene. After cooling to room temperature the product was washed several times with water and the organic phase freed of benzene. There were obtained 270 grams of crude product as a colorless liquid which was separated by distillation.

Thereby there were obtained 205 grams of monoadduct as a viscous, colorless distillate (B.P.$_{0.4}$ 168°–172° C) and 51 grams of the dimer compound as the viscous, colorless sump.

The analysis of the monoadduct gave the empirical formula $C_{16}H_{34}O_4$ and the following values

|  | % C | % H |
|---|---|---|
| Found | 66.4 | 12.0 |
| Calculated | 66.2 | 11.8 |

The analysis of the dimer compound gave the empirical formula $C_{28}H_{58}O_5$ and the following values

|  | % C | % H |
|---|---|---|
| Found | 71.1 | 12.4 |
| Calculated | 70.9 | 12.4 |

In a manner analogous to the processes in Examples (a) and (b) there were carried out the following reactions.

EXAMPLE (c)

The reaction of 51.2 grams of 1,2-epoxyoctane with 26.0 grams of ethylene glycol catalyzed with 1.0 gram of sodium methylate resulted in 70.4 grams of crude ethylene glycol-(2-hydroxyoctyl) ether which after distillation was obtained in an amount of 51.8 grams as a colorless liquid, B.P.$_2$ 105°–110° C.

The analysis of the ether gave the empirical formula $C_{10}H_{22}O_3$ and the following values

|  | % C | % H |
|---|---|---|
| Found | 63.5 | 11.8 |
| Calculated | 63.2 | 11.7 |

EXAMPLE (d)

36.8 grams of 1,2-epoxydodecane were dissolved in 124 ml of benzene and brought to reaction in the presence of 0.12 gram of boron trifluoride etherate with 37.2 grams of ethylene glycol. There were obtained 47.1 grams of a crude addition product which after a vacuum distillation gave 35.3 grams of monoadduct as a colorless liquid, B.P.$_{0.2}$ 138°–142° C. The analysis of the product resulted in the empirical formula $C_{11}H_{30}O_3$ and the following values

|  | % C | % H |
|---|---|---|
| Found | 68.5 | 12.4 |
| Calculated | 68.2 | 12.3 |

EXAMPLE (e)

178 grams of a technical mixture of dodecene-1 and tetradecene-1 (iodine number 143) were dissolved in 200 ml of chloroform and treated at 60° C with 152 grams of a 55 weight percent aqueous peracetic acid. The mixture was allowed to react 3 hours at 60° C, the organic phase washed neutral with water and the chloroform drawn off under reduced pressure. There were obtained 192 grams of a crude 93 weight percent epoxidate (titration against HBr in glacial acetic acid) that could be further worked up without purification.

38.7 grams of this epoxidate were reacted with 21.2 grams of diethylene glycol catalyzed with 0.65 gram of sodium methylate. There were obtained 53.5 grams of crude product as a yellowish viscous oil.

EXAMPLE (f)

36.8 grams of 1,2-epoxydodecane were dissolved in 124 ml of benzene and brought to reaction in the presence of 0.35 grams of boron trifluoride with 117 grams of tetraethylene glycol. There were obtained 70.8 grams of the crude adduct as a colorless, viscous liquid.

EXAMPLE (g)

36.8 grams of 1,2-epoxydodecene were dissolved in 124 ml of benzene and brought to reaction with 180 grams of polyethylene glycol 300 in the presence of 0.54 gram of boron trifluoride etherate. There were obtained 94 grams of the crude adduct as a colorless, viscous liquid.

EXAMPLE (h)

53.6 grams of 1,2-epoxyoctadecane were reacted with 21.2 grams of diethylene glycol in the presence of 0.3 gram of sodium methylate. There were obtained 68 grams of the crude adduct as a colorless, wax-like substance.

EXAMPLE (i)

53.6 grams of 1,2-epoxyoctadecane were dissolved in 180 ml of benzene and brought to reaction with 63.6 grams of diethylene glycol in the presence of 0.2 gram of boron trifluoride. There were obtained 71 grams of the crude adduct as a colorless, wax-like substance.

EXAMPLE (k)

38 grams of epoxide of the statistical chain length $C_{11}$-$C_{14}$ (produced from an olefin mixture with statistical double bonds of the chain length $C_{11}$-$C_{14}$ and iodine number 145.5) were dissolved in benzene and reacted with 116.5 grams of tetraethylene glycol. There were obtained 71 grams of the crude adduct as a yellow-brown liquid.

EXAMPLE (l)

38.7 grams of the epoxidate of Example (e) consisting of the epoxide of a technical mixture of dodecene-1 and tetradecene-1 (iodine number 143) were reacted with 15.2 grams of 1,2-propylene glycol while catalyzed with 0.65 gram of sodium methylate. There were obtained 45 grams of crude adduct as a weakly yellowish oil.

EXAMPLES OF USE

EXAMPLE 1

100 parts by weight of high pressure polyethylene (Lupolen ®) 2000 H of the company BASF AG were thoroughly mixed in each case with 0.25 part by weight of an antistatic agent of the invention and homogenized on a two-roll mixing mill at 125° C for 5 minutes. The resulting rolled sheets were comminuted and pressed in a frame press within 8 minutes to 1 mm thick sheets.

The evaluation of the antistatic activity of the equipped synthetic resin was carried out by measuring the surface resistance according to DIN 53482 (German Industrial Standard 53482) with the Tera-Ohm-Meter, Type PM 6509 (manufacturer; Philips), whereby contacts of WTW (Wissenschaftlich technische Werkstatten in Weilheim, Bavaria) of Type OFZ 3 were used. In each case two measurements of the antistatic effect were carried out; the first immediately after the formation of the polyethylene sheet as a measure of the antistatic finishing in the processing step and the second after a conditioning time of 24 hours at 45% relative humidity as a measure of the speed of migration of the antistatic agent in the synthetic resin and, in comparison with the named beginning values, as a measure of the change of the antistatic activity with the passage of time.

The following Table 1 contains the measured values obtained with and without the materials of the invention produced according to the above production examples. Table 2 contains the measured values obtained with materials according to the state of the art.

TABLE 1

| Substance According To | | Surface Resistance (in Ohms) | |
|---|---|---|---|
| Ex. | | As Formed | After Conditioning 24 Hours At 45% Relative Humidity |
| | Blank (Without Addition of an Antistatic) | $3 \times 10^{14}$ | $2 \times 10^{14}$ |
| (a) | Crude Product | $2 \times 10^{10}$ | $1 \times 10^{9}$ |
| (a) | Monomer Compound | $5 \times 10^{10}$ | $2 \times 10^{10}$ |
| (a) | Dimer Compound | $6 \times 10^{13}$ | $8 \times 10^{13}$ |
| (a) | Mixture of Monomer and Dimer Compounds (Mixing Ratio About 3:2) | $4 \times 10^{11}$ | $3 \times 10^{10}$ |
| (b) | Crude Product | $1 \times 10^{10}$ | $3 \times 10^{9}$ |
| (b) | Monoadduct | $5 \times 10^{10}$ | $1 \times 10^{10}$ |
| (b) | Diadduct (Sump product) | $2 \times 10^{14}$ | $7 \times 10^{13}$ |
| (b) | Mixture of Mono- and Di-adduct (Sump product, Mixing Ratio About 4:1) | $1 \times 10^{10}$ | $7 \times 10^{9}$ |
| (c) | Distillate | $2 \times 10^{11}$ | $2 \times 10^{10}$ |
| (c) | Crude Product | $2 \times 10^{11}$ | $2 \times 10^{10}$ |
| (d) | Distillate | $9 \times 10^{9}$ | $7 \times 10^{9}$ |
| (d) | Crude Product | $1 \times 10^{12}$ | $2 \times 10^{10}$ |
| (e) | | $2 \times 10^{10}$ | $3 \times 10^{9}$ |
| (f) | | $5 \times 10^{10}$ | $3 \times 10^{9}$ |
| (g) | | $2 \times 10^{11}$ | $5 \times 10^{9}$ |
| (h) | | $2 \times 10^{10}$ | $1 \times 10^{10}$ |
| (k) | | $2 \times 10^{14}$ | $4 \times 10^{10}$ |
| (l) | | $5 \times 10^{11}$ | $6 \times 10^{10}$ |

TABLE 2

| | Surface Resistance (in Ohms) | |
|---|---|---|
| | As Formed | After Conditioning 24 Hours at 45% Relative Humidity |
| For Comparison (State of the Art) $C_{10}H_{21}-\underset{\underset{OH}{\mid}}{CH}-CH_2-N=(C_2H_4OH)_2$ According to US-PS 3 365 435 | $2 \times 10^{12}$ | $2 \times 10^{12}$ |

TABLE 2-continued

|  | Surface Resistance (in Ohms) | |
|---|---|---|
|  | As Formed | After Conditioning 24 Hours at 45% Relative Humidity |
| and US-PS 3 317 505 $CH_3-(CH_2)_{9-11}-\underset{\underset{OH}{\mid}}{CH}-CH_2-N\diagup\hspace{-1em}\diagdown O$  According to US-PS 3 308 111 | $2 \times 10^{14}$ | $9 \times 10^{13}$ |
| $C_{10}H_{21}-\underset{\underset{OH}{\mid}}{CH}-CH_2-O-(CH_2-\underset{\underset{CH_2-O)_3H}{\mid}}{CHOH})$  According to German OS 2 324 888 | $5 \times 10^{13}$ | $2 \times 10^{11}$ |

EXAMPLE 2

The thermal stability of the crude product of Example (b) was investigated with the help of the Mettler thermoanalysis system which permits a simultaneous recording of the weight curve, the differentiated weight curves and the differentiated thermal analysis curves in dependence upon the testing temperature. Thereby the maximum weight decrease is not seen below 376° C and a weak endothermal peak is recognized at 277° C.

According to this result the material possesses an excellent thermal stability and can be added without loss of the activity at high working temperatures.

EXAMPLE 3

Analogous to the test sheets produced in Example 1 in which 0.25 part of antistatically active crude product of Example (b) is worked in sheets of the same kind were hung on a metal rod provided with clasps and dipped continuously 10 times in a 1 liter beaker filled with twice distilled water. Subsequently the samples were allowed to dry free hanging in the air.

The resistance measurements according to DIN 53482 took place shortly before and after the treatment and then in intervalls of several days, in order to ascertain the subsequent migration velocity of the antistatic agent. The results are set forth in subsequent Table 3.

TABLE 3

| Surface Resistance (Average Value of 5 Individual Measurements) Measured in Ohms | | | | | | |
|---|---|---|---|---|---|---|
| As Formed | Measured Immediately After the Water Treatment | 24 Hours After the Water Treatment | 48 Hours After the Water Treatment | 7 Days After the Water Treatment | 10 Days After the Water Treatment | 14 Days After the Water Treatment and Conditioning at 45% Relative Humidity |
| $2 \times 10^{10}$ | $2 \times 10^{10}$ | $1 \times 10^{10}$ | $1 \times 10^{10}$ | $9 \times 10^9$ | $8 \times 10^9$ | $5 \times 10^9$ |

The investigations show that by washing with water the test sheets only lose their antistatic activity to an insignificant extent and can be regenerated again in the course of two weeks to full activity.

EXAMPLE 4.1

25 kg of high pressure polyethylene powder (Lupolen ® 2000 H of BASF AG) were mixed in a mixer for several minutes with 1.31 kg of the antistatic agent made in Example (b) (crude product of Example (b)) in order to make an antistatic containing master batch. The mixture was extruded with the help of a planet roll extruder and the strands obtained were granulated.

EXAMPLE 4.2

19 parts by weight of high pressure polyethylene (Lupolen ® 2430 H of BASF AG) and 1 part by weight of the master batch described in Example 4.1 were mixed and homogenized on a two-roll mixing roll at 125° C. The rolled sheet was comminuted and at 150° C pressed in a frame press to a 1 mm thick sheet. The content of antistatic agent amounted to 0.25 weight percent. The surface resistance was measured according to Example 1.

| Surface Resistance In Ohms | |
|---|---|
| As Formed | After Conditioning at 45% Relative Air Humidity During 24 Hours |
| $5 \times 10^9$ | $1 \times 10^9$ |

EXAMPLE 4.3

19 parts by weight of high pressure polyethylene (Lupolen ® 2430 H of BASF AG) and 1 part by weight of the master batch described in Example 4.1 were homogeneously mixed. In the customary manner there were produced films having a thickness of 50 microns. The following surface resistance values were measured.

| Surface Resistance In Ohms | |
|---|---|
| As Formed | After Conditioning at 45% Relative Air Humidity During 24 Hours |
| $4 \times 10^{10}$ | $5 \times 10^9$ |

EXAMPLE 5

In a manner analogous to Example 4.2 there were produced test sheets from high pressure polyethylene and the master batch described in Example 4.1. The test sheets contained 0.15 or 0.20 weight percent of the antistatic agent according to Example (b) (crude product of Example (b)). The test objects obtained were investigated as to the long time activity of the antistatic treatment. In order to simulate mechanical use of the samples, as f.i. in housekeeping by a dust rag, the samples were wiped off in regular sequence. The wiping off took place respectively with a new dry cloth which was turned after each 10 wiping processes. The samples were stored open at relative air humidity between 25 and 45%.

The surface resistances were determined respectively before and after the wipings. The measurements took place in a manner corresponding to Example 1 according to DIN 53482 and are set forth in Table 4.

TABLE 4

|  | Content of Antistatic Agent In Weight Percent | |
|---|---|---|
|  | 0.15 | 0.20 |
| 24 Hours | $2 \times 10^{10}$ | $1 \times 10^{10}$ |
| 1 Week | $2 \times 10^8$ | $6 \times 10^8$ |
| 2 Weeks | $2 \times 10^8$ | $3 \times 10^8$ |
| 3 Weeks | $3 \times 10^8$ | $3 \times 10^8$ |
| 4 Weeks | $3 \times 10^8$ | $3 \times 10^8$ |
| Wiped off | $2 \times 10^9$ | $2 \times 10^9$ |
| 5 Weeks | $2 \times 10^9$ | $1 \times 10^9$ |
| Wiped off | $6 \times 10^9$ | $4 \times 10^9$ |
| 6 Weeks | $2 \times 10^9$ | $1 \times 10^9$ |
| Wiped off | $3 \times 10^9$ | $2 \times 10^9$ |
| 7 Weeks | $5 \times 10^9$ | $3 \times 10^9$ |
| Wiped off | $3 \times 10^{10}$ | $1 \times 10^{10}$ |
| 9 Weeks | $6 \times 10^9$ | $2 \times 10^9$ |
| Wiped off | $2 \times 10^{10}$ | $6 \times 10^9$ |
| 12 Weeks | $4 \times 10^{10}$ | $8 \times 10^9$ |
| Wiped off | $9 \times 10^{10}$ | $2 \times 10^{10}$ |
| 15 Weeks | $3 \times 10^{10}$ | $8 \times 10^9$ |
| Wiped off | $4 \times 10^{10}$ | $1 \times 10^{10}$ |
| 18 Weeks | $7 \times 10^{10}$ | $1 \times 10^{10}$ |
| Wiped off | $1 \times 10^{11}$ | $3 \times 10^{10}$ |
| 21 Weeks | $8 \times 10^9$ | $2 \times 10^9$ |
| Wiped off | $2 \times 10^{10}$ | $6 \times 10^9$ |

The results of the investigation show that the test objects even after long storage time and many wipings lost only an insignificant antistatic effect.

EXAMPLE 6

Low pressure polyethylene (Lupolen ® 6041 D of BASF AG) or polypropylene (Hostalen ® PPN 1060 of Hoechst AG) were thoroughly mixed with the amounts of the crude product of Example (b) set forth in Table 5 below and homogenized on a two-roll mixing roll at 165° C (polyethylene) or 180° C (polypropylene) for 5 minutes. The rolled sheets formed were comminuted and pressed at 180° C (polyethylene) or 200° C (polypropylene) in a frame press within 8 minutes to form 1 mm thick sheets.

The evaluation of the antistatic properties of are thus equipped synthetic resins took place in a manner corresponding to Example 1 by DIN 53482.

TABLE 5

| Polymer with Antistatic Agent (in Weight %) | Surface Resistance (in Ohms) After Conditioning at 45% Relative Humidity | | |
|---|---|---|---|
|  | After 1 Day | After 7 Days | After 14 Days |
| LUPOLEN ®6041 D |  |  |  |
| 0 | $5 \times 10^{14}$ |  |  |
| 0.5 | $4 \times 10^{12}$ | $4 \times 10^{11}$ | $3 \times 10^9$ |
| 1.0 | $2 \times 10^{10}$ | $1 \times 10^9$ | $7 \times 10^8$ |
| HOSTALEN ® PPN 1060 |  |  |  |
| 0 | $3 \times 10^{14}$ |  |  |
| 0.5 | $9 \times 10^{12}$ | $5 \times 10^{12}$ | $1 \times 10^{12}$ |
| 1.0 | $2 \times 10^{12}$ | $3 \times 10^{10}$ | $4 \times 10^9$ |

EXAMPLE 7

100 parts by weight plasticizer containing polyvinyl chloride of the following recipe

| Polyvinyl Chloride (Vinnol ® P 70 of Wacker-Chemie, Munich) | 67 Parts by Weight |
|---|---|
| Polyvinyl Chloride (Solvic ® 336 of Deutsche Solvay-Werke, Dusseldorf | 33 Parts by Weight |
| Dioctyl Phthalate | 50 Parts by Weight |
| Stabilizer (Irgastab ® BC 206 of Ciba-Geigy) | 1 Part by Weight | were in every case homogenized with 3 parts by weight of an antistatic agent by means of a rapid mixer. With the help of a drawing apparatus a 1 mm thick film was coated on a glass plate from the paste formed and gelled for 3 minutes at 180° C in a drying cabinet. The necessary test objects for measuring the surface resistance were subsequently cut out.

The evaluation of the antistatic properties took place according to Examples 1 based on the following test results.

TABLE 6

| Additive According To Example | Surface Resistance (in Ohms) | |
|---|---|---|
|  | As Formed | After a Conditioning Time of 24 Hours at 45% Relative Air Humidity |
| — Without additive | $4 \times 10^{11}$ | $3 \times 10^{11}$ |
| (b) Crude Product | $1 \times 10^{10}$ | $7 \times 10^9$ |
| (b) Monomer Compound | $7 \times 10^9$ | $6 \times 10^9$ |
| (b) Dimer Compound | $8 \times 10^9$ | $6 \times 10^9$ |
| (d) Crude Product | $6 \times 10^9$ | $4 \times 10^9$ |
| (b) | $2 \times 10^9$ | $2 \times 10^9$ |
| (g) | $2 \times 10^9$ | $3 \times 10^9$ |
| (i) | $2 \times 10^9$ | $2 \times 10^8$ |
| (k) | $6 \times 10^9$ | $4 \times 10^9$ |

EXAMPLE 8

Corresponding to Example 7 100 parts by weight of plasticizer containing polyvinyl chloride was treated in each case with 3 parts of the antistatic agents named in Table 7 below and test objects produced. These were subjected to the static heat test whereby they were left for fixed times in a circulatory oven and subsequently their coloration was evaluated according to the data given in Table 7.

TABLE 7

| Antistatic Agent | Duration of the Treatment at 180° C in Minutes | | |
|---|---|---|---|
|  | 0 | 10 | 20 |
| None (For Comparison) | 0 | 0 | 0–1 |
| Commercial PVC Antistatic Agent Based on Quaternary Ammonium Compound (Catafor CA 80 of Glovers Chemicals Ltd., Leeds, Great Britain) | 0 | 6 |  |
| Material of Example 1 | 0 | 0 | 0–1 |

Evaluation Data
0 = no coloration
1 = slight coloration
2 = slight to moderate coloration
3 = moderate coloration
4 = strong coloration
5 = very strong coloration
6 = black coloration

EXAMPLE 9

Corresponding to example 4.1 there was produced a master batch from 24 kilograms of said high pressure polyethylene powder, 1.35 kilograms of said antistatic agent and 0.68 kilograms of a silica filler (produced by acid precipitation from an aqueous alkalimetal silicate solution with a surface area of about 200 to 300 m²/g, measured by the known BET-Method with liquid nitrogen and an average primary particle size of 5 to 50 nanometers). The master batch had a content of 5% by weight of antistatic agent and 2.5% by weight of silica filler.

Now was produced a film of 50 microns thickness by the method described in example 4.3 from a composition of 24 parts by weight of said polyethylene and 1 part by weight of the master batch described above.

The film had a content of 0.2% by weight of antistatic agent and of 0.1% weight of silica filler. The film had a measured surface resistance of $7 \times 10^{10}$ ohms as formed and of $7 \times 10^9$ ohms after conditioning at 45% relative air humidity during 24 hours and showed an excellent antiblocking effect.

The compositions can comprise, consist essentially of or consist of the materials set forth.

The antistatic agents are used in an amount sufficient to have an antistatic effect on the polymer.

What is claimed is:

1. A composition comprising a compound of the formula

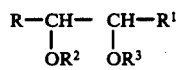

where
one of R and $R^1$ is alkyl and the other R and $R^1$ is hydrogen or alkyl and the sum of carbon atoms in R and $R^1$ is 4 to 30,
$R^2$ is hydrogen or, if $R^3$ is hydrogen then $R^2$ is the group

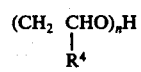

where $n$ is 1 to 10,
$R^3$ is hydrogen or, if $R^2$ is hydrogen than $R^3$ is the group

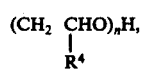

and
$R^4$ is hydrogen or methyl and a thermoplastic synthetic resin which is a polyolefin, polyvinyl chloride, polystyrene, polyvinyl acetate, polymethyl methacrylate, styrene-acrylonitrile copolymer or ethylene-vinyl acetate copolymer, said compound being present in an amount sufficient to impart antistatic properties to said resin.

2. A composition according to claim 1 wherein the thermoplastic synthetic resin is a polyolefin or polyvinyl chloride.

3. A composition according to claim 2 wherein the thermoplastic synthetic resin is polyethylene.

4. A composition according to claim 2 wherein the thermoplastic synthetic resin is polypropylene.

5. A composition according to claim 2 wherein the thermoplastic synthetic resin is polyvinyl chloride.

6. A composition according to claim 1 wherein R is alkyl and $R^1$ is hydrogen.

7. A composition according to claim 1 wherein R and $R^1$ are both alkyl.

8. A composition according to claim 1 wherein the sum of carbon atoms in R and $R^1$ is 4 to 20.

9. A composition according to claim 1 wherein $R^4$ is hydrogen.

10. A composition according to claim 1 wherein $n$ is 1 to 4.

11. A composition according to claim 6 wherein R is alkyl of 8 to 18 carbon atoms and $R^1$ is hydrogen.

12. A composition according to claim 1 containing 0.01 to 20 parts of said compound per 100 parts of resin.

13. A composition according to claim 1 wherein said thermoplastic synthetic resin is polyethylene, polypropylene, polystyrene, polyvinyl chloride, polyvinyl acetate, polybutadiene, polymethylmethacrylate, ethylene-propylene copolymer, ethylene-vinyl acetate copolymer or styrene-acrylonitrile copolymer.

14. A composition according to claim 13 wherein the polymer is polyethylene, polypropylene or polyvinyl chloride.

15. A composition according to claim 1 containing 0.1 to 20 parts of said compound per 100 parts of said thermoplastic resin.

16. A composition according to claim 15 containing 0.1 to 40 parts of silica.

17. A composition according to claim 1 containing 0.01 to 5% of said compound based on said thermoplastic synthetic resin.

18. A composition according to claim 17 containing 0.1 to 3% of said compound.